United States Patent [19]

Onodera et al.

[11] Patent Number: 4,954,326
[45] Date of Patent: Sep. 4, 1990

[54] PREPARATION OF CRYSTALLINE ALUMINOSILICATE ZEOLITE, AND ITS PRODUCT

[75] Inventors: Tamio Onodera; Tokuji Sakai; Yasuo Yamasaki; Koji Sumitani, all of Matsuyama, Japan

[73] Assignee: Teijin Petrochemical Industries, Ltd., Tokyo, Japan

[21] Appl. No.: 380,723

[22] Filed: Jul. 12, 1989

Related U.S. Application Data

[63] Continuation of Ser. No. 891,063, Jul. 31, 1986, abandoned, which is a continuation of Ser. No. 757,928, Jul. 23, 1985, abandoned, which is a continuation of Ser. No. 495,825, May 18, 1983, abandoned.

[30] Foreign Application Priority Data

May 19, 1982 [JP] Japan ................... 57-83240

[51] Int. Cl.$^5$ ............................................. C01B 33/28
[52] U.S. Cl. .................................................... 423/328
[58] Field of Search ............... 423/326, 328, 329, 330; 502/60, 77

[56] References Cited

U.S. PATENT DOCUMENTS

| | | | |
|---|---|---|---|
| 3,702,886 | 11/1972 | Argauer et al. | 423/328 |
| 4,175,114 | 11/1979 | Plank et al. | 423/329 |
| 4,257,885 | 3/1981 | Grose et al. | 210/691 |
| 4,275,047 | 6/1981 | Whittam | 423/329 |
| 4,420,467 | 12/1983 | Whittam | 423/328 |
| 4,524,055 | 6/1985 | Onodera et al. | 423/328 |

FOREIGN PATENT DOCUMENTS

| | | | |
|---|---|---|---|
| 7512644 | 5/1976 | Netherlands | 423/328 |
| 7512645 | 5/1976 | Netherlands | 423/328 |

*Primary Examiner*—Robert L. Stoll
*Assistant Examiner*—R. Bruce Breneman
*Attorney, Agent, or Firm*—Sherman and Shalloway

[57] ABSTRACT

A process for producing a crystalline aluminosilicate zeolite characterized by having (a) a silica/alumina mole ratio of from 10 to 100, (b) X-ray lattice distances d shown in Table A of the specification, and (c) a specific n-hexane adsorption, under limited measuring conditions, of at least 0.07 g/g, which comprises maintaining a silica source, an alumina source, and a zeolite selected from zeolites ZSM-5 and zeolites having said characteristics, in an aqueous solution containing 1 to 200 millimoles, per gram of said zeolite, of an alkali metal hydroxide under such temperature, pressure and time conditions as to produce a crystalline aluminosilicate zeolite; and a crystalline aluminosilicate zeolite characterized by having aforesaid properties (a) to (c) and (d) a (2-methylpentane/cyclohexane) adsorption ratio of from 1.1 to 1.6.

14 Claims, 2 Drawing Sheets

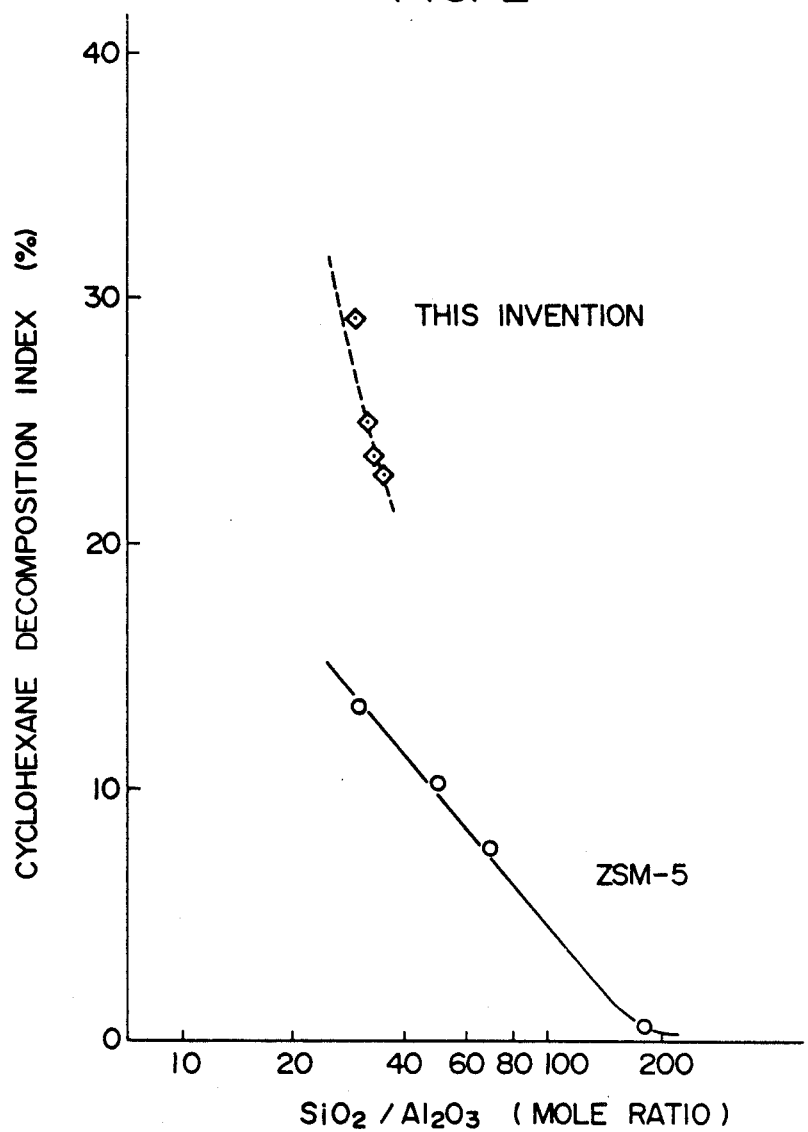

4,954,326

PREPARATION OF CRYSTALLINE ALUMINOSILICATE ZEOLITE, AND ITS PRODUCT

This is a continuation of application Ser. No. 06/891,063 filed July 31, 1986, whereby in turn is a continuation of application Ser. No. 757,928, filed July 23, 1985, which is in turn a continuation of application Ser. No. 495,825, filed May 18, 1983, which in turn are all now abandoned.

This invention relates to an improved process for producing crystalline aluminosilicate zeolites. More specifically, this invention pertains to a process for producing crystalline aluminosilicate zeolites having certain characteristics in increased yields from zeolite ZSM-5 or its analogous compound as seed zeolites.

The crystalline aluminosilicate zeolite will sometimes be referred to simply as "zeolite" in the present specification.

The "zeolite ZSM-5" or "ZSM-5" as used in the present specification and the appended claims, denotes a crystalline aluminosilicate zeolite having an X-ray diffraction pattern characterized by the X-ray lattice distances shown in Table 1 of U. S. Patent Specification No. 3,702,886.

Zeolites are characterized by containing a cation such as a Na, K or H ion and having a three-dimensional network crystalline structure composed principally of $SiO_4$ and $AlO_4$ in which regular tetrahedrons composed of Si atoms and Al atoms crosslinked through oxygen atoms are highly oriented. They are produced naturally or are synthesized.

Zeolites have a uniform size and contain numerous pores. By utilizing these characteristics, they are used as molecular sieves and also find extensive use as catalysts or carriers in various chemical reactions.

Since synthetic zeolites are very uniform and highly pure and have various desirable excellent properties, many synthetic zeolites and processes for their production have been proposed heretofore.

Zeolites having a high silica content as shown by a $SiO_2/Al_2O_3$ mole ratio of at least 10 have high stability and a unique acidity, and exhibit high activity when used as catalysts for conversion of hydrocarbons, for example their selective adsorption, cracking, hydrocracking, isomerization, alkylation, etc. Many such zeolites having a high silica content, mainly ZSM series zeolites, have been proposed up to date (see, for example, U.S. Pat. Nos. 3,702,886; 3,709,979; 3,832,449; 4,016,245 and 4,061,724.).

Zeolites having a high silica content are produced usually by reacting a silica source, an alumina source, an alkali metal cation and another cation to be used in combination with it, and the structure and properties of the resulting zeolites differ depending upon the kind and combination of the other cation.

Heretofore, many proposals have been made to use certain amines or organic ammonium salts as the other cation to be used in combination with the alkali metal cation. Examples include tetra-n-propyl ammonium hydroxide (U.S. Pat. No. 3,702,886), n-butyl alcohol and ammonia (British Patent No. 2,018,232), tri-n-propylamine and a propyl halide (British Patent No. 2,058,033), and alcoholamines (Japanese Laid-Open Patent Publication No. 17920/1981).

However, zeolites synthesized and used commercially are limited in species, and among them, ZSM series zeolites, particularly ZSM-5, are produced and used in great quantities because of their excellent activity and stability as catalyst.

As described in detail in U.S. Pat. No. 3,702,886, ZSM-5 is synthesized by the presence of an alkali metal cation (specifically, a sodium ion) and a specified organic ammonium ion (specifically, a tetran-propyl ammonium ion). The ZSM-5 so produced is highly crystalline and has a high silica/alumina mole ratio and the characteristic X-ray lattice distances described in the aforesaid patent specification. ZSM-5 has many uniform pores of a definite size, and this partly characterizes the properties of ZSM-5.

Synthetic zeolites having a definite structure and properties are formed depending upon the combination of the cations used for their production, and ZSM-5 zeolite can be obtained in a definite structure and properties by the manufacturing process described above.

The production of ZSM-5, however, requires the use of a large amount of expensive and corrosive organic ammonium salts or amines as a source of organic cations, as described in the above-cited U.S. Pat. No. 3,702,886 and British Patent No. 2,058,033. Hence, much expenditures go into the corrosion inhibition of the reaction equipment and the disposal of the waste materials, and the cost of production of ZSM-5 becomes very high. Moreover, long periods of usually from several days to about one week are required to produce ZSM-5, and the production efficiency is poor.

The present inventors made extensive investigations in order to develop a process for producing a crystalline aluminosilicate zeolite having substantially the same basic crystal structure as ZSM-5 with good efficiency within short periods of time without using organic ammonium salts or amines having the aforesaid defects. These investigations have now led to the discovery that if ZSM-5 or its analogous compound is used instead of the organic ammonium salts or amines, zeolites having basically the same crystal structure as ZSM-5 and a high degree of crystallinity can be produced in increased yields within short periods of time.

Thus, according to this invention, there is provided a process for producing a crystalline aluminosilicate zeolite characterized by having (a) a silica/alumina mole ratio of from 10 to 100, (b) X-ray lattice distances d shown in Table A of the specification, and (c) a specific n-hexane adsorption under limited measuring conditions of at least 0.07 g/g, which comprises maintaining a silica source, an alumina source and a zeolite selected from zeolites ZSM-5 and zeolites having said characteristics, in an aqueous solution containing 1 to 200 millimoles, per gram of said zeolite, of an alkali metal hydroxide under such temperature, pressure and time conditions as to produce a crystalline aluminosilicate zeolite.

The essential feature of the process of this invention is to produce zeolites without substantially using organic ammonium salts or amines required in the conventional production of ZSM-5; in other words, to produce zeolites in the presence of ZSM-5 or a zeolite produced in advance by the process of this invention, in the substantial absence of an organic cation derived from such organic ammonium salts or amine.

According to this invention, by simply using a silica source, an alumina source and an aqueous solution of an alkali metal hydroxide which are usually employed in the synthesis of zeolites, and a starting zeolite selected from zeolites ZSM-5 and zeolites produced by the process of this invention as starting materials, zeolites can be synthesized in very high yields corresponding to several times to ten and several times under preferred conditions the amount of the starting zeolite.

In the process of this invention, any silica sources normally used in zeolite production can be used Examples are silica powder, colloidal silica, watersoluble silicon compounds and silicic acid. As the silica powder, precipitated silica produced from alkali metal silicates such as aerosil silica, fuming silica and silica gel, are preferred The colloidal silica is available in various particle sizes, and colloidal silica having a particle diameter of 10 to 50 microns is advantageously utilized. Examples of the water-soluble silicon compounds are alkali metal silicates, such as water glass, sodium silicate and potassium silicate, which contain 1 to 5 moles, especially 2 to 4 moles, of $SiO_2$ per mole of the alkali metal oxide. Colloidal silica or water glass is especially preferred as the silica source.

On the other hand, the alumina source may be any of those which are generally used in the production of zeolites, for example alumina, mineral acid salts of aluminum, and aluminates. Specific examples include hydrated aluminas, or aluminas capable of being hydrated, such as colloidal alumina, pseudoboehmite, boehmite, $\gamma$-alumina, $\alpha$-alumina and $\beta$-alumina trihydrate; aluminum chloride, aluminum nitrate and aluminum sulfate; and sodium aluminate and potassium aluminate. Of these, sodium aluminate and aluminum salts of mineral acids are preferred.

It is also possible to use aluminosilicate compounds, for example naturally occurring feldspars, kaolin, acid clay, bentonite, and montmorillonite, as a common source of supplying silica and alumina. The aforesaid silica source and/or alumina source may partly or wholly be replaced by the aluminosilicate.

The amount of the silica source in the starting mixture used in this invention is generally 0.1 to 200 millimoles, preferablY 1 to 100 millimoles, preferably 5 to 80 millimoles, calculated as $SiO_2$ per gram of the starting zeolite. The amount of the alumina source is generally 0.01 to 20 millimoles, preferably 0.1 to 10 millimoles, more preferably 0.5 to 5 millimoles, calculated as $Al_2O_3$ per gram of the starting zeolite. The mixing ratio between the silica source and the alumina source is not critical. Generally, it is preferred to adjust the $SiO_2/Al_2O_3$ mole ratio to a range of 1 to 200, especially 5 to 100. If this mole ratio is lower than 1, the desired zeolite cannot be obtained If it exceeds 200, the degree of crystallinity of the products decreases.

Sodium hydroxide and potassium hydroxide are especially preferred as the alkali metal hydroxide They may be used either alone or in combination.

The alkali metal hydroxide is used in an amount of 1 to 200 millimoles, preferably 5 to 100 millimoles, more preferably 10 to 80 millimoles, per gram of the starting zeolite. Relative to the silica source and the alumina source, the alkali metal hydroxide is used in such an amount that the alkali metal hydroxide/$(SiO_2+Al_2O_3)$ mole ratio is generally from 0.1 to 10, preferably from 0.2 to 5, more preferably from 0.3 to 1.

Usually, the alkali metal hydroxide is used in the form of an aqueous solution. Conveniently, the concentration of the alkali metal hydroxide in the aqueous solution is generally 1 to 100 millimole, preferably 5 to 50 millimoles, more preferably 10 to 40 millimoles, per mole of water in the reaction system.

The starting zeolite ZSM-5 which can be a seed of the resulting zeolite in the process of this invention is a known zeolite which can be obtained in a known manner by subjecting a combination of an alkali metal cation and a certain organic cation together with a silica source and an alumina source to hydrothermal synthesis conditions in an alkaline aqueous solution. For example, U.S. Pat. No. 3,702,886 discloses a method in which tetra-n-propyl ammonium hydroxide is used as a source of the organic cation; British Patent No. 2,018,232, a method in which n-butyl alcohol and ammonia are used; British Patent No. 2,058,033, a method in which tri-n-propylamine and a n-propyl halide are used; and Japanese Laid-Open Patent Publication No. 17920/1981, a method in which an alcoholamine is used. The synthetic zeolites obtained by these methods are usually washed thoroughly with water, and calcined at a temperature of, for example, 300° to 700° C., preferably 400° to 600° C., to remove the organic cation. However, the ZSM-5 used in the process of this invention, may be one in which the organic cation has been removed by calcination, or one in which the organic cation remains.

The ZSM-5 zeolite as a starting material in this invention may also be one which, after the aforesaid calcining operation, is further subjected to a known ion-exchange process whereby an ion originally existing in the zeolite is partly or wholly exchanged with another cation, for example a monovalent cation such as a lithium, silver or ammonium cation, a divalent alkaline earth metal cation such as a magnesium, calcium or barium cation, a cation of a Group VIII metal such as cobalt, nickel, platinum or palladium, or a trivalent cation such as a rare earth metal cation.

Furthermore, the object of this invention can also be achieved by using a zeolite obtained by this invention as a starting zeolite instead of the ZSM-5 zeolite described above. Such a starting zeolite may be in the form of a slurry immediately after synthesis, or a powder obtained by separation from the filtrate followed by drying and calcining steps. The starting zeolite may also be one subjected to ion exchange with such a metal cation as exemplified above with regard to the ZSM-5 zeolite.

According to the process of this invention, the aforesaid silica source, alumina source, alkali metal hydroxide, zeolite and water are mixed in the proportions described above, and the mixture is maintained under temperature, pressure and time conditions sufficient to form a crystalline zeolite.

In addition to adjusting the proportions of the silica source, alumina source, alkali metal hydroxide and water to the aforesaid values, it is advantageous to use the silica source, alumina source and alkali metal hydroxide in the starting mixture in such proportions that $SiO_2$, $Al_2O_3$ and a hydroxyl ion (OH—) based on the alkali metal satisfy the following relationship:

$SiO_2/Al_2O_3$ = 1–200, preferably 5–100, more preferably 10–80

$OH^-/(SiO_2 + Al_2O_3)$ = 0.1–10, preferably 0.2–5, more preferably 0.3–1

$OH^-/H_2O$ = 0.001–0.1, preferably 0.005–0.05, more preferably 0.01–0.04

The temperature at which the zeolite synthesis reaction is carried out is not critical, and may be substantially the same as that employed for the production of conventional ZSM-5 zeolites. Advantageously, the temperature is usually at least 90° C., preferably 100° to 250° C., more preferably 120° to 200° C.

According to the process of this invention, the rate of reaction is markedly increased over conventional processes, and a reaction period of usually 30 minutes to 7 days, preferably 1 hour to 2 days, especially preferably 2 hours to 1 day, suffices for crystallization. The reaction pressure is an elevated pressure ranging from the autogenous pressure in an autoclave to a higher pressure. Generally, the reaction is carried out under autogenous pressure, and it is also possible to carry out the reaction in an atmosphere of an inert gas such as nitrogen gas.

Zeolite synthesis in accordance with the process of this invention may be performed by a batchwise procedure in which a starting mixture containing all of the aforesaid materials is charged into a reactor and reacted under the aforesaid conditions. Or it may be performed by a continuous method in which a slurry of a silica source and a slurry of an alumina source are continuously fed into a reactor charged in advance with an aqueous solution of the alkali metal hydroxide and the starting zeolite, and the reaction is carried out stepwise.

Or it is possible to take out a part of the product obtained by the aforesaid process, and feed a fresh supply of the aqueous alkali metal hydroxide solution, the silica source and the alumina source, batchwise or continuously to the aforesaid product, thereby reacting them further.

The starting mixture is heated to the desired temperature, and if required with stirring, maintained at this temperature until a zeolite is formed.

After the zeolite crystals are formed, the reaction mixture is cooled to room temperature, filtered, and washed with water until the ion conductivity of the washing reaches 50 $\mu$ U/cm or below. Then, the crystals are separated. If required, the crystals are maintained at 50° C. or higher for 5 to 24 hours under atmospheric or reduced pressure in order to dry them.

Thus, according to the process of this invention, a zeolite can be synthesized in an amount several times to ten and several times, under preferred conditions, the amount of the starting zeolite by a batch procedure by simply using zeolite ZSM-5 or the zeolite obtained by the process of this invention in addition to the silica source, alumina source and aqueous alkali metal solution which are usually employed in the synthesis of zeolites. In a continuous operation, the zeolite can be synthesized in an amount at least 100 times the amount of the starting zeolite.

The resulting zeolite contains an alkali metal ion as a cation, and can be subjected to ion exchange in a manner known per se. For example, it may be contacted with an aqueous solution of ammonium chloride to substitute an ammonium ion for the cation site. When the ion-exchanged zeolite is further calcined, the ammonium ion can be converted to a hydrogen ion to form a zeolite in an activated state.

It is also within the domain of the present invention to exchange the alkali metal ion of the zeolite of this invention partly or wholly with another cation. Examples of cations which can be exchanged include monovalent metal cations such as a lithium, potassium or silver ion; alkaline earth metal cations such as a magnesium, calcium or barium ion; divalent transition metal cations such as a manganese, iron, cobalt, nickel, copper or zinc cation; noble metal cations such as a rhodium, palladium or platinum cation; and rare earth metal cations such as a lanthanum or cerium cation.

Exchange with the various cations exemplified above can be effected by known methods. For example, the zeolite is brought into contact with an aqueous or non-aqueous medium containing an aqueous solution containing the desired cation. This contacting treatment may be carried out batchwise or continuously.

The resulting zeolite may be calcined at a temperature of 100° to 600° C., preferably 300° to 500° C., for 5 to 40 hours, preferably 8 to 24 hours. This calcination is also within the scope of this invention.

The process of this invention described hereinabove gives a crystalline aluminosilicate zeolite characterized by having
(a) a silica/alumina mole ratio of from 10 to 100,
(b) X-ray lattice distances d shown in Table A of the specification, and
(c) a specific n-hexane absorption, under limited measuring conditions, of at least 0.07 g/g.

The zeolite produced by the process of this invention will now be described in more detail partly in conjunction with the accompanying drawings in which

BRIEF DESCRIPTION OF THE DRAWINGS

FIG. 2 is a graph obtained by plotting the correlation between the SiO mole ratio and the cyclohexane decomposition index of the zeolite obtained in Examples 1 and 2 given hereinafter.

Figure 1:
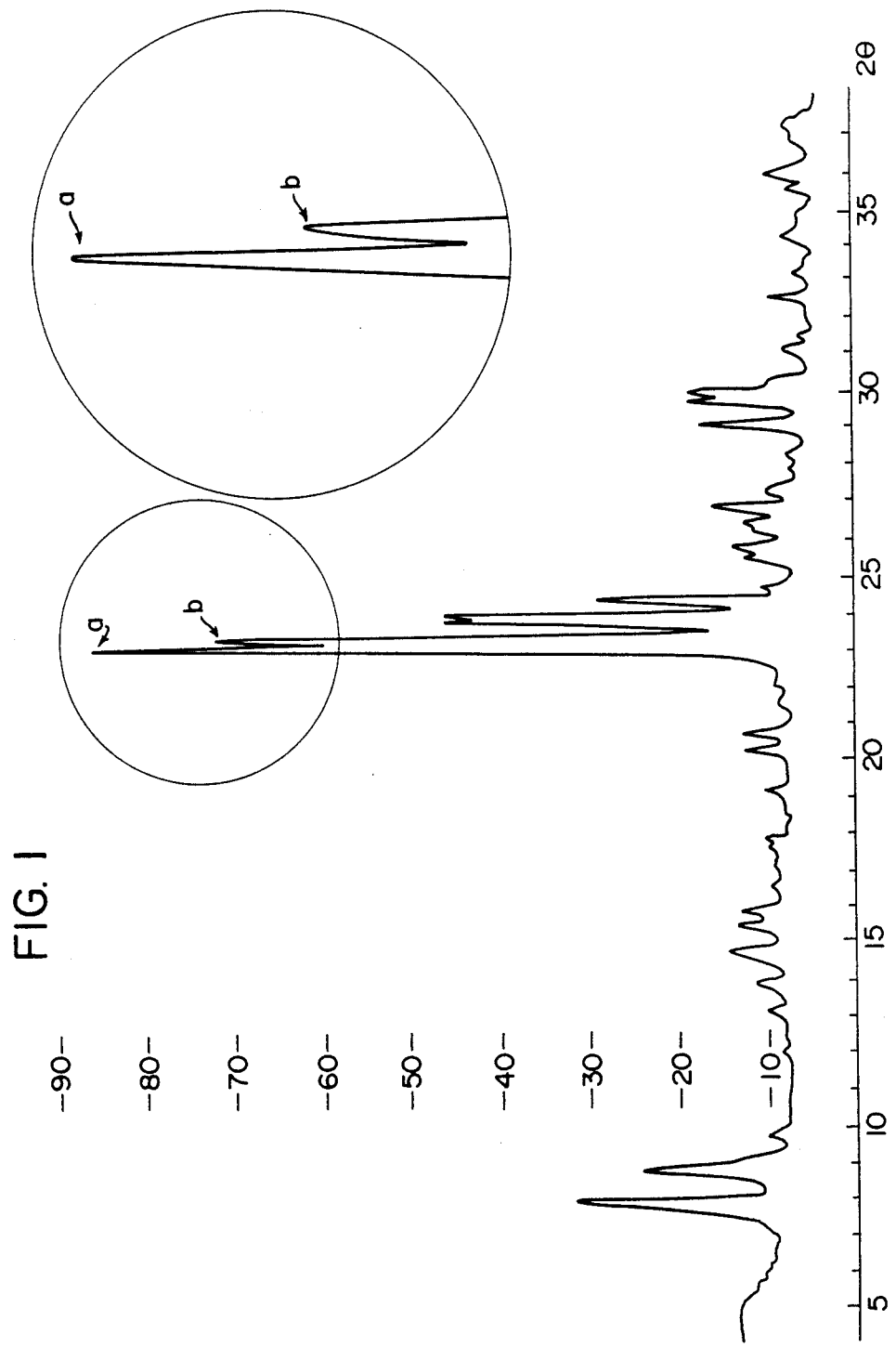
FIG. 1 is an X-ray diffraction chart of a typical zeolite in accordance with this invention.

The zeolite provided by this invention has a $SiO_2/Al_2O_3$ mole ratio in the range of from 10 to 100, preferably 15 to 70, more preferably, 20 to 50.

The zeolite provided by the invention has the X-ray lattice distances shown in Table A below. The present inventors have found as a result of detailed comparative studies that some differences exist between the X-ray diffraction chart of the zeolite of the invention and that of ZSM-5. One great difference is that the X-ray lattice distance d(Å) which gives the strongest peak in ZSM-5 is 3.5 (2$\theta$=23.14) according to the above-cited U.S. Pat. No. 3,702,886, whereas in the zeolite of this invention, the strongest peak is branched and observed at d(Å)=3.86 and 3.83 (2$\theta$=23.05 and 23.25) (see peaks a and b in FIG. 1). Another great difference is that one peak observed at d(Å)=3.00 (2$\theta$=29.76) in ZSM-5 is observed as a bifurcated peak at d(Å)=3.00 (2$\theta$=29.75) (peak c of FIG. 1). The latter-mentioned bifurcated peak is observed in most of the zeolites of this invention, if not in all.

The X-ray lattice distances d(Å) of the zeolite of this invention and their relative intensities are shown below. The relative intensity (I/Io) is relative intensity of each peak when the intensity (Io) of a peak at d(Å)=3.86 (2$\theta$=23.05) is taken as 100.

TABLE A

| X-ray lattice distance, d(Å) | Diffraction angle, 2$\theta$ | Relative intensity (I/Io) |
| --- | --- | --- |
| 11.26 | 7.85 | 37 |
| 10.11 | 8.75 | 24 |
| 9.83 | 9.00 | 6 |
| 9.12 | 9.70 | 1 |
| 7.51 | 11.80 | 1 |
| 6.78 | 13.05 | 4 |
| 6.05 | 14.65 | 9 |

TABLE A-continued

| X-ray lattice distance, d(Å) | Diffraction angle, 2θ | Relative intensity (I/Io) |
| --- | --- | --- |
| 5.74 | 15.45 | 7 |
| 5.61 | 15.80 | 8 |
| 5.41 | 16.40 | 2 |
| 5.00 | 17.75 | 6 |
| 4.65 | 19.10 | 4 |
| 4.39 | 20.25 | 8 |
| 4.28 | 20.75 | 14 |
| 4.11 | 21.65 | 4 |
| 4.04 | 22.05 | 7 |
| 3.86 | 23.05 | 100 |
| 3.83 | 23.25 | 75 |
| 3.75 | 23.70 | 45 |
| 3.74 | 23.80 | 53 |
| 3.66 | 24.30 | 33 |
| 3.61 | 24.65 | 5 |
| 3.50 | 25.45 | 7 |
| 3.46 | 25.75 | 10 |
| 3.36 | 26.50 | 19 |
| 3.33 | 26.80 | 10 |
| 3.28 | 27.20 | 4 |
| 3.26 | 27.35 | 1 |
| 3.06 | 29.15 | 16 |
| 3.00 | 29.75 | 18 |
| 2.98 | 29.95 | 18 |
| 2.96 | 30.20 | 8 |

Furthermore, the two very strong peaks at d(Å)=3.86 and 3.83 characteristic of the zeolite of this invention has the relationship that when the intensity (Io) of the peak at d(Å)=3.86 (2θ=23.05) is taken as 100, the relative intensity (I/Io) of the peak at d(Å)=3.83 (2θ=23.25) is at least 70, typically 73 to 78.

Another important characteristic of the zeolite provided by this invention over ZSM-5 and other similar zeolites is that it has an extremely high specific adsorption of n-hexane which is at least 0.07 g/g.

The specific adsorption of n-hexane is a value measured in accordance with the definition given hereinafter.

The specific n-hexane adsorption is a factor relating to the pore volume of the zeolite. Larger specific adsorption values mean larger pore volumes of the channels of the zeolite. There is a natural upper limit to the specific adsorption of n-hexane. The upper limit to the specific n-hexane adsorption of the zeolite provided by this invention is generally about 0.1 g/g, typically about 0.0S g/g. Accordingly, the zeolite provided by this invention preferably has a specific n-hexane adsorption in the range of from 0.07 to 0.09 g/g.

Another property of the zeolite provided by this invention is expressed by a (2-methylpentane/cyclohexane) adsorption ratio which is a value to be measured by the method described hereinafter. The zeolite provided by this invention may have a (2-methylpentane/cyclohexane) adsorption ratio of generally from 1.1 to 1.6, preferably from 1.2 to 1.5, more preferably from 1.25 to 1.45.

The (2-methylpentane/cyclohexane) adsorption ratio is a factor relating to the pore diameter of the channels of the zeolite. Large adsorption ratios mean that cyclohexane molecules having a large cross section are difficult of entering the channels of the zeolite, whereas 2-methylpentane molecules having a smaller cross section than cyclohexane are easy of entering the channels of the zeolite. Accordingly, when a zeolite having a channel pore diameter represented by an adsorption ratio within the above range is used as a catalyst, it exhibits unique shape selectivity, and becomes a novel catalyst having a high industrial value.

The zeolite provided by this invention also has unique chemical activity. For example, the zeolite in the activated state has a cyclohexane decomposition index ratio (the activity of the zeolite relative to the activity of ZSM-5 having the same $SiO_2/Al_2O_3$ mole ratio when each zeolite is contacted with cyclohexane) of at least 1.1, preferably at least 1.5, more preferably at least 1.7.

The term "in the activated state", as used in the present specification and the appended claims, means that most of alkali metal ions contained in the zeolite provided by this invention immediately after preparation are substituted by hydrogen ions in accordance with known methods. In other words, it means that at least 70%, preferably at least 90%, of cation exchange sites based on the alumina of the zeolite are substantially occupied by hydrogen ions, whereby zeolite in the activated state is obtained (the zeolite in this state may sometimes be referred to as "H-form zeolite").

Generally, zeolites have an approximately definite activity (especially acidity) according to its $SiO_2/Al_2O_3$ mole ratio. However, the zeolite provided by the present invention has the characteristic that it has a higher activity than ZSM-5 having nearly the same $SiO_2/Al_2O_3$ mole ratio. If the cyclohexane decomposing activity of a certain standard ZSM-5 is taken as 1, that activity of the zeolite provided by the invention having nearly the same $SiO_2/Al_2O_3$ mole ratio as the ZSM-5 is shown by a cyclohexane decomposition index ratio of at least 1.1, preferably at least 1.5. The present inventors presume that it is due to the larger pore diameter (size) and the higher acid strength in the pores of the zeolite provided by this invention than ZSM-5. The upper limit of the cyclohexane decomposition index ratio of the zeolite provided by this invention is generally 3, preferably 2.5.

The "specific n-hexane adsorption", the "(2-methylpentane/cyclohexane) adsorption ratio" and the "cyclohexane decomposition index ratio", which are indices showing the characteristic features of the zeolite provided by this invention, are defined and measured as follows:

(1) Specific n-hexane adsorption

This is defined as the weight of n-hexane adsorbed on 1 g of zeolite under the following fixed conditions, and measured as follows:

A pelletized zeolite obtained by calcination in an electric muffle furnace at 450° C. for 8 hours is precisely weighed by using a spring balance in an adsorption device. Then, the inside of an adsorption tube is evacuated ($10^{-1}$ mmHg) for 1 hour. n-Hexane in gaseous form is introduced into the adsorption tube until the pressure reaches 50±1 mmHg, and maintained at room temperature (20±1° C.) for 2 hours. The weight of the adsorbed n-hexane can be calculated from the difference between the lengths of the spring balance before and after adsorption.

(2) (2-Methylpentane/cyclohexane) adsorption ratio

This ratio is expressed by the ratio of the weight of 2-methylpentane adsorbed on 1 g of zeolite to that of cyclohexane adsorbed on 1 g of zeolite under fixed conditions. The weights of the 2-methylpentane and cyclohexane adsorbed on zeolite are measured in the same way as in (1) above.

(3) Cyclohexane decomposition index ratio (to be sometimes abbreviated C.D.R. value hereinafter)

The cyclohexane decomposition index ratio is defined as the ratio of the cyclohexane decomposition index of the H-form zeolite obtained by this invention to that of an H-form ZSM-5 zeolite in the activated state having the same silica/alumina mole ratio as the zeolite of the invention.

The cyclohexane decomposition index is measured by calcining a pelletized zeolite having a size of 10 to 20 mesh and containing 50% by weight of γ-alumina in an electric furnace at 450° C. for 8 hours, loading a predetermined weight of the calcined zeolite in a fixed bed-type reactor, and feeding cyclohexane and hydrogen (hydrogen/cyclohexane mole ratio=2/1) at a temperature of 350° C. and a weight hourly space velocity (WHSV) of 2 hour$^{-1}$ (based on the total weight) under ambient pressure. The amount of cyclohexane converted (per 100 parts by weight of the feed) under these conditions is the cyclohexane decomposition index. WHSV is a value calculated from the following formula.

$$WHSV = \frac{\text{Weight of the hydrocarbon feed fed per unit time}}{\text{Weight of the catalyst}}$$

The zeolite provided by this invention has the aforesaid characteristics and the following chemical composition.

$$xM_{2/n}O \cdot Al_2O_3 \cdot ySiO_2 \quad (I)$$

This formula represents the zeolite in the form of an oxide in an anhydrous condition. M represents at least one cation having a valence of n, x is 0.5 to 4, and y is 10 to 100.

Immediately after production, M in the zeolite represents an alkali metal, particularly sodium. It can be exchanged with a cation such as a hydrogen ion, an ammonium ion or another metal ion by ion exchange methods usually known. Even the zeolites in accordance with this invention in which M is exchanged with any other cation than a sodium ion essentially have the requirements of the zeolite of the invention described above.

In the formula (I) above, x is a measure of the amount of a cation bonded to the zeolite, and is 0.5 to 4, preferably 0.9 to 3.

A zeolite, i.e. a crystalline aluminosilicate, as a model, consists basically of a combination of tetrahedrons of silica and alumina and has such a structure that the charge of the alumina tetrahedrons is neutralized by the presence of cations in the structures.

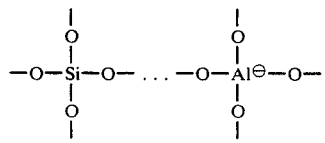

Theoretically, therefore, x showing the amount of the cation in formula (I) representing the zeolite is 1 which is equimolar to alumina. In practice, however, synthesized zeolites usually contain cation precursors which cannot be removed by usual washing. It is rare that according to actual analytical data of synthesized zeolites, x becomes 1. Thus, "x" in formula (I) is understood as representing the amount (moles) of total ions in the purified synthetic zeolite which include cations based on alumina, and cation precursors existing in the structure after usual washing.

The zeolite provided by this invention has X-ray lattice distances different from those of ZSM-5, a slightly larger pore diameter than ZSM-5, and different chemical activity from ZSM-5 (generally the zeolite of the invention has high reaction activity and selectivity for the desired reaction). Hence, it is expected to be used in applications which ZSM-5 zeolite does not find.

Because of the aforesaid excellent properties, the zeolite of this invention can be used widely as a catalyst for the conversion reactions of aromatic hydrocarbons such as the disproportionation, isomerization, alkylation, transalkylation and dealkylation of alkylbenzenes and alkylnaphthalenes, and reforming and cracking of naphtha or as a selective adsorbent or as a catalyst carrier.

As a catalyst in these conversion reactions, the zeolite of the invention may be used directly. Depending upon the reaction to be catalyzed, it may also be used after supporting thereon a catalytically active metals or metal oxides which are identical with, or different from, the metal cation present in the cation site. Examples of the catalytically active metals or metal oxides used for this purpose are alkaline earth metals such as magnesium, calcium, strontium and barium, lanthanide metals such as lanthanum and cerium, Group VIII metals in the periodic table such as iron, cobalt, nickel, ruthenium, rhodium, palladium, osmium, iridium and platinum, and the oxides of these.

Such catalytically active metals or metal oxides may be deposited on the zeolite by methods known per se, for example, by the method described in European Patent Application Specification No. 0018498. Instead of depositing the catalytically active metals or metal oxides on the zeolite provided by the invention, it is also possible to deposit the metals or metal oxides on a conventional refractory oxide carrier, preferably alumina, mix the supported metals or metal oxides with the zeolite provided by the invention, mold the mixture into a desired shape such as pellets or tablets, and then use the molded product in the intended reaction.

Since the zeolite provided by the invention can be advantageously used particularly in the isomerization or transalkylation of alkylbenzenes and alkylnaphthalenes, these reactions will be described below somewhat specifically.

When the zeolite provided by this invention is used in such isomerization or transalkylation, the zeolite is conveniently one in the activated state in which at least 50%, preferably at least 70%, of the cation sites are occupied by hydrogen ions. In these reactions, the zeolite of the invention may be used in the form of a fine powder, or as required, in the form of pellets, tablets and other desired shapes obtained by molding it in a usual manner. Molding of the zeolite is carried out in a customary manner by mixing it with a synthetic or natural refractory inorganic oxide used ordinarily as a binder for zeolite catalysts, such as silica, alumina, silica-alumina, kaolin, or silica-magnesium, molding the mixture into the desired shape, and then calcining the molded product. Advantageously, the amount of the zeolite in the molded product is generally 1 to 100% by weight, preferably 10 to 90% by weight, based on the weight of the molded product.

Prior to use, the catalyst so prepared may be treated at a temperature of 200° to 600° C., preferably 250° to 550° C., in a reducing atmosphere such as hydrogen gas.

(1) Isomerization

The zeolite provided by this invention can be advantageously used as a catalyst for isomerizing alkylbenzenes and alkylnaphthalenes, for example dialkylbenzenes such as xylenes, methylethylbenzenes and diethylbenzene, trialkylbenzenes such as trimethylbenzene and ethylxylenes, and dialkylnaphthalenes such as dimethylnaphthalenes. More specifically, it is suitable for use as a catalyst in the isomerization of an isomeric mixture of xylenes not in a thermodynamically equilibrium state, isomerization of an isomeric mixture of trimethylbenzenes not in a thermodynamically equilibrium state, isomerization of m-xylene to p-xylene, isomerization of 1,3,5-trimethylbenzene to 1,2,4-trimethylbenzene, isomerization of 1,6-dimethylnaphthalene to 2,6-dimethylnaphthalene, isomerization of 2,7-dimethylnaphthalene to 2,6-dimethylnaphthalene, isomerization of 2,3-dimethylnaphthalene to 2,6- or 2,7-dimethylnaphthalene.

In particular, the zeolite of this invention is characteristic in that it shows unique reactivity not found in conventional catalysts in the isomerization reaction of dialkylnaphthalenes. It has previously been thought that in the isomerization of a dialkylnaphthalene, only the shift of the alkyl group from the α-position to the β-position or from the β-position to the α-position on the same ring is possible. It has now been found in accordance with this invention that the use of the zeolite provided by this invention makes it possible to shift the alkyl substituent from one ring to another (for example, from the 3-position to the 6- or 7-position) and shift the alkyl substituent from the α-position (1-position) to the α-position (4-position) or from the β-position (2-position) to the β-position (3-position) on the same ring. With the zeolite of this invention, this shifting reaction proceeds selectively without side-reactions. The zeolite provided by this invention can thus be used advantageously as a catalyst for a reaction of converting 2,7-dimethylnaphthalene having little availability to 2,6-dimethylnaphthalene which is industrially valuable, or a reaction of isomerizing 2,3-dimethylnaphthalene into 2,6- or 2,7-dimethylnaphthalene.

The isomerization reaction can be carried out by contacting alkylbenzenes or alkylnaphthalenes with a bed of the zeolite of the invention at a temperature generally in the range of 250° to 500° C., preferably 300° to 400° C. The weight hourly space velocity (WHSV) in this catalytic reaction can be varied according to the type of the starting material to be fed. In the case of alkylbenzenes which have a relatively small molecular size, the WHSV can be in the range of 1 to 100, preferably 5 to 40, based on the zeolite. In the case of alkylnaphthalenes having a relatively large molecular size, the time of contact of the alkylnaphthalenes with the zeolite is advantageously prolonged by adjusting WHSV to a range of 0.05 to 20, preferably 0.1 to 5, based on the zeolite.

The isomerization reaction can be performed generally at atmospheric pressure to 20 kg/cm²·G, preferably 1 to 10 kg/cm²·G. A diluent such as nitrogen or hydrogen may be supplied to the feedstock. Supplying of hydrogen is industrially advantageous because it will prolong the life of the catalyst activity. The suitable amount of hydrogen used in this case is 0.1 to 100 moles, preferably 1 to 50 moles, per mole of the feedstock.

In performing the isomerization reaction, the contacting of the feedstock with the catalyst may be effected in a fixed fed or fluidized bed reactor. Preferably, the former is used.

The isomerization reaction may be carried out either in the liquid phase or in the vapor phase.

(2) Transalkylation

Transalkylation is a reaction of shifting the alkyl group between two molecules of the same or different types of alkylbenzenes or alkylnaphthalenes. Specifically, the following reaction of shifting the methyl group can be cited as an example.

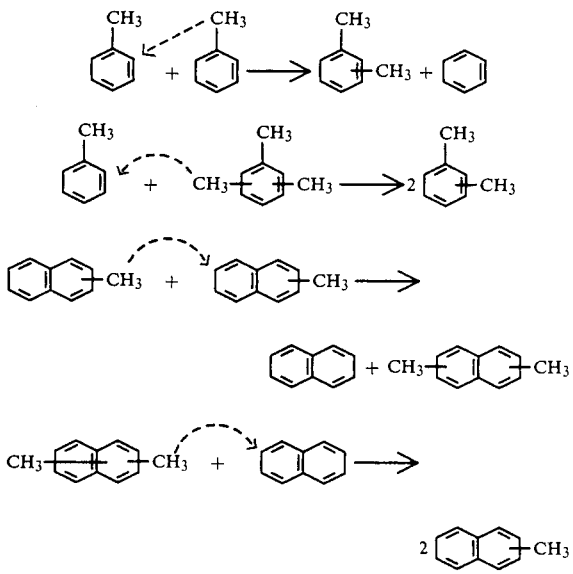

Toluene, a mixture of toluene and trimethylbenzenes, monomethylnaphthalene or a mixture of naphthalene and dimethylnaphthalenes used in the transalkylation reaction needs not to be pure, and may be diluted with other inert aromatic hydrocarbons and used as feedstocks. For example, a mixture of toluene and trimethylbenzenes so diluted suitably contains at least 10% by weight, preferably at least 30% by weight, of toluene, and at least 15% by weight, preferably at least 40% by weight, of trimethylbenzenes.

In performing the transalkylation reaction using the zeolite provided by this invention, the feedstock is passed through a catalyst bed composed of the zeolite of this invention at a temperature of generally 250° to 550° C., preferably 300° to 450° C. WHSV in this reaction may be varied depending upon the kind of the feedstock. In the case of alkylbenzenes having relatively low bulkiness in its molecular size, WHSV may be in the range of 0.1 to 50, preferably 0.5 to 10, based on the zeolite. In the case of relatively bulky alkylnaphthalenes, WHSV is suitably in the range of 0.05 to 20, preferably 0.1 to 5, based on the zeolite.

The transalkylation reaction may be carried out 5 at atmospheric pressure to 20 kg/cm²·G, preferably 1 to 10 kg/cm²·G. A diluent such as nitrogen or hydrogen may be supplied to the feedstock. Supplying of hydrogen is industrially advantageous because it will prolong the life of the catalyst activity. The suitable amount of hydrogen used in this case is 0.1 to 100 moles, preferably 1 to 50 moles, per mole of the feedstock.

In performing the transalkylation reaction, the contacting of the feedstock with the catalyst may be effected in a fixed or fluidized bed reactor. Preferably, the former is used.

In the aforesaid isomerization reaction and transalkylation reaction catalyzed by the zeolite provided by the present invention, the zeolite shows much higher activity and selectivity than in the same reactions on conventional catalysts. Hence, the amount of the zeolite catalyst can be decreased and milder reaction conditions can be used. The industrial advantage of using the zeolite of the invention is great.

The following Examples illustrate the present invention in detail.

EXAMPLE 1

Four ZSM-5 zeolites having different silica/alumina mole ratios were synthesized by the method disclosed in the specification of U.S. Pat. No. 3,766,093.

In synthesizing them, tri-n-propylamine and n-propyl bromide were added as a source of an organic ammonium ion. The product obtained was filtered, thoroughly washed with water, dried in an electric oven at 100° C. for 16 hours and then at 200° C. for 8 hours, and further calcined at 500° C. for 16 hours under an air current. The resulting products had a silica/alumina mole ratio of 32.8 (zeolite A-1), 50.1 (zeolite A-2), 71.9 (zeolite A-3), and 181 (zeolite A-4), respectively.

EXAMPLE 2

(A) Synthesis of zeolite 1n accordance with this invention (A) Sodium hydroxide (special reagent grade made by Wako Pure Chemicals, Co., Ltd.; 10.53 g)was dissolved in 210 ml of pure water. To the resulting alkaline aqueous solution were added 3.11 g of aluminum sulfate. 16-18 hydrate (special reagent grade made by Wako Pure Chemicals, Co., Ltd.) as an alumina source. Furthermore, as a silica source, 69.4 g of silica sol (Cataloid S-30L, a product of Catalysts & Chemicals Industries Co., Ltd.; 30 wt.% $SiO_2$) was added to form a gel. The gel was then charged into a 300 ml stainless steel autoclave, and 6.9 g of ZSM-5 zeolite A-3 prepared in Example 1 was added.

The proportions of the starting materials per gram of ZSM-5 were 50 millimoles of $SiO_2$, 0.71 millimole of $Al_2O_3$ and 38.04 millimoles of NaOH. In terms of mole ratios, $SiO_2/Al_2O_3=70.4$, $OH^-/(SiO_2+Al_2O_3)=0.75$, and $OH^-/H_2O=1.8\times 10^{-2}$.

With gentle stirring, the charged starting mixture was reacted at 180° C. under autogenous pressure for 6 hours. The reaction product was separated by filtration, and washed thoroughly until the washing had an ion conductivity of not more than 50 $\mu U$/cm. It was dried overnight at 90° C. and its then weighed. It was 10.3 g which was 1.5 times the weight of the ZSM-5 zeolite charged (the product is designated zeolite B). The zeolite B had an $SiO_2/Al_2O_3$ mole ratio of 24.0, and showed an X-ray diffraction pattern having the characteristics shown in Table A given hereinabove. $2\theta=23.14$ which gives the strongest peak in ZSM-5 zeolite clearly separated into $2\theta=23.00$ and $2\theta=23.25$ as shown in FIG. 1.

(B) In an alkaline aqueous solution prepared by dissolving 9.4 g of sodium hydroxide in 188 ml of pure water was dissolved 5.56 g of aluminum sulfate 16-18 hydrate as an alumina source. Furthermore, 92 g of silica sol (30 wt.% $SiO_2$) was added as a silica source to prepare a gel. The gel was charged into a 300 ml stainless steel autoclave, and then 7.0 g of ZSM-5 zeolite A-3 was suspended in the gel.

The proportions of the starting materials charged per gram of ZSM-5 zeolite were 65.7 millimoles of $SiO_2$, 1.26 millimoles of $Al_2O_3$, and 33.6 millimoles of NaOH. In terms of mole ratios, $SiO_2/Al_2O_3=52.1$, $OH^-/(SiO_2+Al_2O_3)=0.50$, and $OH^-/H_2O=1.7\times 10^{-2}$.

The reaction was then performed by the same method and under the same conditions as in section (A) above. The reaction mixture was washed with water and dried. The weight of the dried product was found to be 22.5 g which was 3.2 times the weight of the ZSM-5 zeolite charged (the resulting zeolite is designated zeolite C).

This zeolite C had a $SiO_2/Al_2O_3$ mole ratio of 34.1, and showed an X-ray diffraction pattern having the characteristics shown in Table A given hereinabove.

(C) The procedure of section (B) was carried out except that zeolite C ($SiO_2/Al_2O_3$ mol ratio=34) obtained in section (B) above was used instead of the ZSM-5 zeolite A-3. The reaction mixture was washed with water and dried. The weight of the dried product (zeolite D) was found to be 22.2 g which was 3.2 times the weight of the zeolite C charged.

The zeolite D had a $SiO_2/Al_2O_3$ mole ratio of 29.2, and showed an X-ray diffraction pattern having the characteristics shown in Table A.

(D) To an alkaline aqueous solution prepared by dissolving 6.0 g of sodium hydroxide in 120 ml of pure water was added 5.34 g of aluminum sulfate 16-18 hydrate as an alumina source. Further, 59.4 g of silica sol was added as a silica source to prepare a gel. The gel (one-third of the entire weight) was charged into a 300 ml stainless steel autoclave, and 3.0 g of a fine powder of ZSM-5 zeolite used in section (A) above was added.

With gentle stirring, the starting materials were reacted at 180° C. under autogenous pressure for 6 hours. Then, another one-third portion of the gel was added, and reacted similarly at 180° C. under autogenous pressure for 6 hours. The remaining gel was added, and reacted under the same conditions.

The proportions of the starting materials charged per gram of ZSM-5 zeolite were 99.0 millimoles of $SiO_2$, 2.83 millimoles of $Al_2O_3$, and 50.0 millimoles of NaOH. In terms of mole ratios, $SiO_2/Al_2O_3=35.0$, $OH^-/(SiO_2+Al_2O_3)=0.49$, and $OH^-/H_2O=2.2\times 10^{-2}$.

The reaction mixture was taken out, and filtered. The separated product was washed fully with pure water until the washing had an ion conductivity of not more than 50 $\mu U$/cm. The washed product was dried overnight at 90° C., and weighed. Its weight was found to be 20.4 g which was 6.8 times the weight of the ZSM-5 zeolite charged. (The resulting zeolite is designated zeolite E).

The zeolite E had a $SiO_2/Al_2O_3$ mole ratio of 35.3, and exhibited an X-ray diffraction pattern having the characteristics shown in Table A above.

EXAMPLE 3

Zeolites A-1, A-3, B, C, D and E were each molded into a size of 20 mesh, and calcined in an electric muffle furnace at 450° C. for 8 hours. About 0.5 g of each of the calcined zeolite was placed on a spring balance suspended within an adsorption tube. After evacuating the inside of the adsorption tube for 1 hour, the weight of the zeolite was precisely weighed from the elongation of the spring. Then, n-hexane, 2-methylpentane or cyclohexane filled in a gas holder was introduced into the adsorption tube until the pressure of the inside of the tube reached 50±1 mmHg. It was maintained at room temperature (20±1 °C.) for 2 hours, and then the length of the spring balance was measured. The amount of each of these gas adsorbed on the zeolite was calculated from the elongation of the spring balance after adsorption.

The amount of the gas adsorbed on the zeolite can be obtained as follows:

$$V = \frac{W_2 - W_1}{W_1}$$

V: the amount of the gas adsorbed per gram of the zeolite
$W_1$: the weight of the zeolite before adsorption
$W_2$: the weight of the zeolite after adsorption Table 1 summarizes the specific adsorptions of n-hexane, 2-methylpentane and cyclohexane, $V_{n-H}$, $V_{2-MP}$, and $V_{CH}$) and the (2-methylpentane/cyclohexane) adsorption ratios, defined by $V_{2-MP}/V_{CH}$), of the zeolites.

TABLE 1

| Zeolite | SiO$_2$/Al$_2$O$_3$ (mole ratio) | Specific adsorption | | | $\frac{V_{2-MP}}{V_{CH}}$ |
|---|---|---|---|---|---|
| | | $V_{n-H}$ | $V_{2-MP}$ | $V_{CH}$ | |
| A-1 | 32.8 | 0.095 | 0.058 | 0.053 | 1.09 |
| A-3 | 71.9 | 0.091 | 0.059 | 0.053 | 1.11 |
| B | 24.0 | 0.087 | 0.051 | 0.034 | 1.50 |
| C | 34.1 | 0.077 | 0.040 | 0.028 | 1.43 |
| D | 29.2 | 0.077 | 0.044 | 0.029 | 1.52 |
| E | 35.3 | 0.073 | 0.038 | 0.026 | 1.46 |

It is seen from the results tabulated above that the zeolites in accordance with this invention have a specific adsorption of n-hexane ($V_{n-H}$) (whose molecules are most slender) which is close to that of ZSM-5, and show specific selectivity for 2-methylpentane whose molecules are somewhat bulky among C$_6$ paraffins.

EXAMPLE 4

The powdery zeolites A-1, A-2, A-3, A-4, B, C, D and E obtained in Examples 1 and 2 were each converted to H-form zeolites.

Specifically, each zeolite was subjected to ion exchange at 70° C. for 16 hours using 5 ml, per unit weight of zeolite, of a 5% by weight aqueous solution of ammonium chloride, and this operation was performed twice. Then, the ion-exchanged zeolite was fully washed with water, dried in an electric dryer at 100° C. for 16 hours and then at 200° C. for 8 hours, and calcined at 450° C. for 16 hours in an atmosphere of air in an electric muffle furnace. Analysis of the sodium content of the zeolite showed that in the zeolite after being subjected to the aforesaid procedure, more than 90% of its cation sites were occupied by protons.

The H-form zeolite so obtained was mixed fully with chromatographic alumina gel (smaller than 300 mesh) in a weight ratio of 1:1, and the mixture was molded into a size of 10 to 20 mesh. The molded article was calcined in an electric muffle furnace at 450° C. for 8 hours in an atmosphere of air, and 4 g of the calcined product was filled in a fixed bed-type reaction tube kept at atmospheric pressure. The temperature of the catalyst bed was adjusted to 350° C., and then 8 g/hr of cyclohexane and hydrogen (hydrogen/cyclohexane mole ratio=2/1) were fed into the reaction tube. Thus, the cyclohexane decomposition index was examined.

The cyclohexane decomposition index ratios (C.D.R. values) of the zeolites are shown in Table 2. The cyclohexane decomposition index of ZSM-5 having an arbitrary silica/alumina mole ratio, which serves as a standard, was determined from the correlation between the silica/alumina mole ratio and the cyclohexane decomposition index in the catalysts obtained in Example 1. FIG. 2 gives this correlation, and indicates that the cyclohexane decomposition ratio of the zeolite of this invention shown by the broken line is higher than that of ZSM-5 shown by the solid line. It is clearly seen from Table 2 that the zeolites of this invention have a C.D.R. ratio well over 1.

TABLE 2

| Zeolite | SiO$_2$/Al$_2$O$_3$ mole ratio | Cyclohexane decomposition index | C.D.R. |
|---|---|---|---|
| A-1 | 32.8 | 13.5 | 1.0 |
| A-2 | 50.1 | 10.4 | (base) |
| A-3 | 71.9 | 8.0 | |
| A-4 | 18.1 | 0.8 | |
| B | 24.0 | 29.5 | 2.0 |
| C | 34.1 | 23.7 | 1.9 |
| D | 29.2 | 25.0 | 1.8 |
| E | 35.3 | 23.0 | 1.8 |

EXAMPLE 5

In this example, transalkylation was carried out for obtaining xylene from toluene and 1,2,4-trimethylbenzene using the zeolite C of this invention (silica/alumina mole ratio=34.1) and the zeolite A-1 as a comparison (silica/alumina mole ratio=32.8).

Each of these zeolites was converted to H-form zeolite by the same method as described in Example 4, and fully mixed with chromatographic alumina gel (smaller than 300 mesh) in a weight ratio of 1:1. The mixture was molded into a size of 10 to 20 mesh, and calcined in an electric muffle furnace at 450° C. for 8 hours. Five grams of the calcined zeolite was filled in a fixed bed reaction tube kept under atmospheric pressure. The temperature of the catalyst bed was adjusted to 400° C., and 10 g of a mixture of toluene and 1,2,4-trimethylbenzene in a mole ratio of 1:1 and hydrogen (hydrogen/hydrocarbon mole ratio=1:1) were fed into the reaction tube.

Five hours after the start of feeding of the starting mixture, the product had the composition shown in Table 3.

It is seen that in spite of having higher silica/alumina mole ratio than zeolite A-1, the zeolite C of this invention gives a very large amount of xylene and is therefore effective for transalkylation reaction.

TABLE 3

| | Feed | Product with zeolite C | With zeolite A-1 |
|---|---|---|---|
| Composition (wt. %) | | | |
| C$_5$-paraffin | | 0.6 | 0.6 |
| Benzene | | 2.6 | 1.2 |
| Toluene | 43.4 | 30.9 | 36.9 |
| Xylenes | | 24.0 | 15.2 |
| Trimethylbenzenes | 56.6 | 41.0 | 45.0 |
| C$_{10}{}^+$ aromatics | | 0.9 | 1.1 |
| Conversion of toluene (%) | | 28.9 | 14.9 |
| Conversion of trimethylbenzenes (%) | | 27.5 | 20.5 |

TABLE 3-continued

| | Feed | Product with zeolite C | Product With zeolite A-1 |
|---|---|---|---|
| Yield of xylenes (%) | | 85.2 | 85.5 |

In the above table, the conversion of toluene, the conversion of trimethylbenzenes and the yield of xylenes are defined as follows:

$$\text{Conversion of toluene (\%)} = \frac{\begin{pmatrix}\text{Concentration}\\\text{of toluene in}\\\text{the feed}\end{pmatrix} - \begin{pmatrix}\text{Concentration}\\\text{of toluene in}\\\text{the product}\end{pmatrix}}{\text{Concentration of toluene in the feed}} \times 100$$

$$\text{Conversion of trimethylbenzenes (\%)} = \frac{\begin{pmatrix}\text{Concentration}\\\text{of trimethyl-}\\\text{benzenes in}\\\text{the feed}\end{pmatrix} - \begin{pmatrix}\text{Concentration}\\\text{of trimethyl-}\\\text{benzenes in}\\\text{the product}\end{pmatrix}}{\text{Concentration of trimethyl-benzenes in the feed}} \times 100$$

$$\text{Yield of xylenes (\%)} = \frac{\text{Moles of xylene formed}}{\begin{pmatrix}\text{Moles of}\\\text{toluene}\\\text{consumed}\end{pmatrix} + \begin{pmatrix}\text{Moles of}\\\text{trimethylbenzenes}\\\text{consumed}\end{pmatrix}} \times 100$$

EXAMPLE 6

The zeolite B obtained in Example 2 was treated with an aqueous solution of ammonium chloride in accordance with the method described in Example 4 to convert it to an H-form zeolite. Three grams of the H-form zeolite was dipped in 10 ml of an aqueous solution containing 79.5 mg of chloroplatinic acid hexahydrate, and maintained at 50° C. for 6 hours. Water was evaporated by using a rotary evaporator. The residue was dried in an electric oven at 100° C. for 8 hours and then at 200° C. for 15 hours, and then calcined in an electric muffle furnace at 450° C. 8 hours under an air current to give a zeolite catalyst containing 1% of platinum.

The catalyst was then molded and calcined in accordance with the method described in Example 5. Six grams of the finished catalyst was filled in a fixed bed-type reaction tube. The temperature of the catalyst bed was elevated to 400° C. under a nitrogen current, and then hydrogen gas was introduced to reduce platinum contained in the catalyst at this temperature for 2 hours. Then, the reaction temperature was adjusted to 400° C., and 12 g/hr of a $C_9+$alkyl aromatic hydrocarbon material having the composition shown in Table 4 and hydrogen in a $H_2$/aromatic hydrocarbon mole ratio of 2.6/1 were fed under a pressure of 90 psia. The composition of the product determined 60 hours after the start of supplying the starting material is shown in Table 4.

The results given in Table 4 demonstrate that the catalyst in accordance with this invention has very high activity in the dealkylation reaction of $C_9+$alkyl aromatic hydrocarbons.

TABLE 4

| Composition (wt. %) | Starting material | Product |
|---|---|---|
| $C_5^-$ paraffins | — | 16.56 |
| Benzene | — | 6.52 |
| Toluene | — | 17.95 |
| Xylene | 0.14 | 29.97 |
| Trimethylbenzenes | 52.36 | 26.93 |
| Ethyltoluenes | 4.95 | 0.03 |
| Ethylxylenes | 19.78 | 0.03 |
| Diethylbenzenes | 22.44 | — |
| Durene+ | 0.33 | 1.35 |
| Conversion (%) of trimethylbenzenes | | 48.6 |
| Conversion (%) of ethyltoluenes | | 99.5 |
| Conversion (%) of ethylxylenes | | 99.9 |
| Conversion (%) of diethylbenzenes | | 100.0 |

The conversions given in Table 4 are defined as follows:

$$\text{Conversion of trimethylbenzenes (\%)} = \frac{\begin{pmatrix}\text{Concentration}\\\text{of trimethyl-}\\\text{benzenes in}\\\text{the feed}\end{pmatrix} - \begin{pmatrix}\text{Concentration}\\\text{of trimethyl-}\\\text{benzenes in}\\\text{the product}\end{pmatrix}}{\text{Concentration of trimethyl benzenes in the feed}} \times 100$$

$$\text{Conversion of ethyltoluenes (\%)} = \frac{\begin{pmatrix}\text{Concentration}\\\text{of ethyl-}\\\text{toluenes in}\\\text{the feed}\end{pmatrix} - \begin{pmatrix}\text{Concentration}\\\text{of ethyl-}\\\text{toluenes in}\\\text{the product}\end{pmatrix}}{\text{Concentration of ethyltoluenes in the feed}} \times 100$$

$$\text{Conversion of ethylxylenes (\%)} = \frac{\begin{pmatrix}\text{Concentration}\\\text{of ethyl-}\\\text{xylenes in}\\\text{the feed}\end{pmatrix} - \begin{pmatrix}\text{Concentration}\\\text{of ethyl-}\\\text{xylenes in}\\\text{the product}\end{pmatrix}}{\text{Concentration of ethylxylenes in the feed}} \times 100$$

$$\text{Conversion of diethylbenzenes (\%)} = \frac{\begin{pmatrix}\text{Concentration}\\\text{of diethyl-}\\\text{benzenes in}\\\text{the feed}\end{pmatrix} - \begin{pmatrix}\text{Concentration}\\\text{of diethyl-}\\\text{benzenes in}\\\text{the product}\end{pmatrix}}{\text{Concentration of diethylbenzenes in the feed}} \times 100$$

EXAMPLE 7

In this example, monomethylnaphthalene was synthesized from naphthalene and 1,5-dimethylnaphthalene using the catalyst prepared in Example 6.

Ten grams of the catalyst was filled in a fixed bed-type reaction tube, and reduced in a hydrogen stream at 400° C. for 2 hours. Then, the temperature of the catalyst bed was adjusted to 375° C., 5 g/hr of a starting material consisting of 1 mole of naphthalene and 1 mole of 1,5-dimethylnaphthalene and hydrogen in a hydrogen/hydrocarbon mole ratio of 3/1 were fed into the reaction tube. The composition of the liquid product determined 10 hours after the start of feeding the starting material is shown in Table 5.

In this reaction, the formation of much monomethylnaphthalenes and isomerization of 1,5-dimethylnaphthalene were observed

TABLE 5

|  | Feed (mol %) | Product (mol %) |
| --- | --- | --- |
| Naphthalene | 48.4 | 41.9 |
| α-Methylnaphthalene | — | 4.9 |
| β-Methylnaphthalene | — | 12.7 |
| 1,5-Dimethylnaphthalene | 51.6 | 2.3 |
| 1,6-Dimethylnaphthalene | — | 9.1 |
| 2,6-Dimethylnaphthalene | — | 8.5 |
| 1,7-Dimethylnaphthalene | — | 7.4 |
| 2,7-Dimethylnaphthalene | — | 8.4 |
| 1,8-Dimethylnaphthalene | — | — |
| 1,4-Dimethylnaphthalene | — | — |
| 1,3-Dimethylnaphthalene | — | 2.6 |
| 2,3-Dimethylnaphthalene | — | 1.4 |
| 1,2-Dimethylnaphthalene | — | — |
| Trimethylnaphthalenes | — | 0.7 |
| Conversion of naphthalene (%) |  | 13.4 |
| Conversion of dimethylnaphthalenes (%) |  | 23.1 |
| Yield of methylnaphthalenes (%) |  | 95.7 |

In Table 5, the conversion of naphthalene, the conversion of dimethylnaphthalenes and the yield of methylnaphthalenes are as defined below.

$$\text{Conversion of naphthalene (\%)} = \frac{\left(\begin{array}{c}\text{Concentration} \\ \text{of naphthalene} \\ \text{in the feed}\end{array}\right) - \left(\begin{array}{c}\text{Concentration} \\ \text{of naphthalene} \\ \text{in the product}\end{array}\right)}{\text{Concentration of naphthalene in the feed}} \times 100$$

$$\text{Conversion of dimethylnaphthalenes (\%)} = \frac{\left(\begin{array}{c}\text{Concentration} \\ \text{of dimethyl-} \\ \text{naphthalenes} \\ \text{in the feed}\end{array}\right) - \left(\begin{array}{c}\text{Concentration} \\ \text{of dimethyl-} \\ \text{naphthalenes} \\ \text{in the product}\end{array}\right)}{\text{Concentration of dimethylnaphthalenes in the feed}} \times 100$$

$$\text{Yield of methylnaphthalenes (\%)} = \frac{\text{Moles of methylnaphthalenes formed}}{\left(\begin{array}{c}\text{Moles of} \\ \text{naphthalene} \\ \text{consumed}\end{array}\right) + \left(\begin{array}{c}\text{Moles of di-} \\ \text{methylnaphthalene} \\ \text{consumed}\end{array}\right)} \times 100$$

EXAMPLE 8

The zeolite C obtained in Example 2, (B) was treated with an aqueous solution of ammonium chloride in accordance with the method described in Example 4 to convert it to an H-form zeolite, and then calcined at 450° C. for 8 hours. Fifteen grams of the resulting powdery zeolite was filled in a fixed bed-type reaction tube. The temperature of the catalyst bed was adjusted to 330° C., and the inside of the reaction tube was pressurized to 15 kg/cm²·G with nitrogen. Fifteen grams/hr of a starting material consisting of 1 mole of naphthalene and 1 mole of 1,5-dimethylnaphthalene was fed into the reaction tube and reacted in the liquid phase. The composition of the product determined 24 hours after the starting of feeding the starting material is shown in Table 6.

It is clear that this zeolite shows good activity in a liquid-phase reaction. In the liquid-phase reaction, changes in the activity of the zeolite with time were very little as compared with the vapor-phase reaction.

TABLE 6

|  | Feed (mol %) | Product (mol %) |
| --- | --- | --- |
| Naphthalene | 49.4 | 41.6 |
| α-Methylnaphthalene | — | 3.2 |
| β-Methylnaphthalene | — | 11.5 |
| 1,5-Dimethylnaphthalene | 50.5 | 8.0 |
| 1,6-Dimethylnaphthalene | — | 13.4 |
| 2,6-Dimethylnaphthalene | — | 9.2 |
| 1,7-Dimethylnaphthalene | — | 3.7 |
| 2,7-Dimethylnaphthalene | — | 5.1 |
| 1,8-Dimethylnaphthalene | — | — |
| 1,4-Dimethylnaphthalene | — | — |
| 1,3-Dimethylnaphthalene | — | 1.9 |
| 2,3-Dimethylnaphthalene | — | 1.3 |
| 1,2-Dimethylnaphthalene | — | — |
| Trimethylnaphthalenes | — | 1.1 |
| Conversion of naphthalene (%) |  | 15.8 |
| Conversion of dimethylnaphthalenes (%) |  | 15.6 |
| Yield of methylnaphthalenes (%) |  | 93.6 |

What is claimed is:

1. A process for producing a crystalline aluminosilicate zeolite characterized by having (a) a silica/alumina mole ratio of from 10 to 100, (b) X-ray lattice distances d shown in Table A of the specification, (c) a specific n-hexane adsorption, as measured on a precisely weighed sample of the zeolite which has been calcined at 450° for 8 hours until the pressure reaches 50±1 mm Hg, and maintained at 20±1° C. for 2 hours of at least 0.07 g/g, (d) a (2-methylpentane/cyclohexane) adsorption ratio of from 1.2 to 1.6, and (e) when the intensity ($I_o$) of the X-ray diffraction peak at d(Å)=3.86 is taken as 100, the relative intensity ($I/I_o$) of the X-ray diffraction peak at d(Å)=3.83 is at least 70, which comprises maintaining a silica source, an alumina source, and a seed zeolite selected from the group consisting of zeolite ZSM-5 and zeolites having said characteristics (a)-(e) inclusive, specified above, in an aqueous solution containing 1 to 200 millimoles, per gram of said zeolite, of an alkali metal hydroxide, in such proportions that the silica source, the alumina source and the alkali metal hydroxide satisfy the following mole ratios in terms of $SiO_2$, $Al_2O_3$ and $OH^-$:

$SiO_2/Al_2O_3 = 5-100$ $OH^-/(SiO_2 + Al_2O_3) =$ about 0.5-1 and $OH^-/H_2O = 0.005-0.05$, and under such temperature, pressure and time conditions as to produce a crystalline aluminosilicate zeolite.

2. The process of claim 1 wherein the seed zeolite is zeolite ZSM-5.

3. The process of claim 1 or 2 wherein the amount of the alkali metal hydroxide in the aqueous solution is 5 to 100 millimoles per gram of the seed zeolite.

4. The process of claim 1 wherein the alkali metal hydroxide is sodium hydroxide, potassium hydroxide, or both.

5. The process of claim 1 wherein the proportions of the silica source and the alumina source are such that 0.1 to 200 millimoles of $SiO_2$ and 0.01 to 20 millimoles of $Al_2O_3$ are used per gram of seed zeolite.

6. The process of claim 5 wherein the proportions of the silica source and the alumina source are such that 1 to 100 millimoles of $SiO_2$ and 0.1 to 10 millimoles of $Al_2O_3$ are used per gram of the seed zeolite.

7. The process of claim 1 wherein the silica source is selected from the group consisting of a silica powder, colloidal silica, water-soluble silicon compounds and silica acid.

8. The process of claim 1 wherein the alumina source is selected from the group consisting of alumina, mineral acid salts of aluminum and aluminate salts.

9. The process of claim 1 wherein the aluminosilicate is used as a common source of silica and alumina.

10. The process of claim 1 wherein the temperature is in the range of 90° to 250° C.

11. The process of claim 1 wherein the pressure is at least the autogenous pressure in an autoclave.

12. The process of claim 1 wherein the proportions of the silica source, the alumina source and the alkali metal hydroxide are such that the $SiO_2/Al_2O_3$ mole ratio is from 10 to 80, the $OH^-(SiO_2+Al_2O_3)$ mole ratio is from about 0.5 to 1 and the $OH^-/H_2O$ mole ratio is from 0.01 to 0.04.

13. The process of claim 1 wherein the relative intensity $(I/I_o)$ is 73 to 78.

14. The process of claim 13 wherein the crystalline aluminosilicate zeolite product has a (2-methylpentane/cyclohexane) adsorption ratio of from 1.25 to 1.45.

* * * * *

UNITED STATES PATENT AND TRADEMARK OFFICE
CERTIFICATE OF CORRECTION

PATENT NO. : 4,954,326
DATED : September 4, 1990
INVENTOR(S) : ONODERA, ET AL.

It is certified that error appears in the above-identified patent and that said Letters Patent is hereby corrected as shown below:

Col. 20, claim 1, line 43 delete "OH ;" insert --$OH^-$--.

line 47, delete "OH-", insert --$OH^-$--.

line 49, delete "OH-", insert --$OH^-$--.

Col. 22, claim 12, line 4, delete "OH-", insert --$OH^-$--.

line 5, delete "OH-", insert --$OH^-$--.

Col. 21, claim 7, line 4, delete "silica", insert --silicic--.

Signed and Sealed this

Seventh Day of July, 1992

Attest:

DOUGLAS B. COMER

Attesting Officer          Acting Commissioner of Patents and Trademarks